US00PP35546P2

(12) United States Plant Patent
Van Dijk

(10) Patent No.: US PP35,546 P2
(45) Date of Patent: Dec. 12, 2023

(54) ***ANTHURIUM* PLANT NAMED 'AN2891370'**

(50) Latin Name: ***Anthurium andraeanum* L.**
Varietal Denomination: AN2891370

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,169

(22) Filed: May 4, 2023

(51) Int. Cl.
*A01H 5/02* (2018.01)
*A01H 6/10* (2018.01)

(52) U.S. Cl.
USPC ..... Plt./368

(58) Field of Classification Search
USPC ..... Plt./368
CPC ..... A01H 5/02; A01H 5/00; A01H 6/10
See application file for complete search history.

(56) References Cited

U.S. PATENT DOCUMENTS

PP27,889 P3 * 4/2017 Van Dijk ..... A01H 6/00
Plt./368

* cited by examiner

*Primary Examiner* — June Hwu
(74) *Attorney, Agent, or Firm* — Jondle & Associates, P.C.

(57) ABSTRACT

A new *Anthurium* plant named 'AN2891370' particularly distinguished by having medium glossy and medium blistered, dark purplish-red, oblong-cordate, and durable spathes that retain the original color for a few weeks, medium glossy, dark green, concave, narrowly-long cordate, durable leaves, dark purple spadices with dark purple tips, early and rich flowering continuously throughout the year, and a plant height of 48.0 cm to 53.0 cm is disclosed.

3 Drawing Sheets

Genus and species: *Anthurium andraeanum* L.
Variety denomination: 'AN2891370'.

BACKGROUND OF THE NEW PLANT

The present invention comprises a new and distinct variety of *Anthurium*, botanically known as *Anthurium andraeanum* L., and hereinafter referred to by the variety name 'AN2891370'. The new *Anthurium* plant is a product of a planned breeding program conducted by the inventor in Bleiswijk, the Netherlands. The objective of this breeding program was to create a new plant with a height of 43.0 cm to 48.0 cm having medium blistered, medium glossy, dark purplish-red, oblong-cordate, and durable spathes.

The new variety originated from a cross-pollination made in April 2014 in Bleiswijk, the Netherlands. The female parent was a light purple *Anthurium* pot plant designated '25528-07' (unpatented), and the male parent was a dark purplish-red *Anthurium* pot plant '25414-03' (unpatented).

A single plant was selected from the progeny of the stated cross in December 2015. Asexual reproduction of the new variety by tissue culture in 2019 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 18, 2021 (Application no. 2021/2961), by Applicant who obtained the subject matter disclosed directly from the inventor. 'AN2891370' has not been made publicly available or sold anywhere in the world prior to the effective filing date of this application with the exception of sales or disclosures made one year or less before the effective filing date of this claimed invention by Applicant who obtained 'AN2891370' directly from the inventor.

SUMMARY OF THE INVENTION

The following are the most outstanding and distinguishing characteristics of this new variety when grown under normal horticultural practices in Bleiswijk, the Netherlands:

1) Medium blistered, medium glossy, dark purplish-red, oblong-cordate and durable spathes;
2) Dark purple spadices with dark purple tips;
3) Green, concave, medium glossy, narrowly-long cordate leaves; and
4) Spathes: shape in cross section of middle zone is slightly concave.

DESCRIPTION OF THE PHOTOGRAPHS

This new *Anthurium* plant is illustrated by the accompanying photographs which show the overall plant habit including blooms, buds, and foliage of the plant; the colors shown are as true as can be reasonably obtained by conventional photographic procedures. The photographs are of a 52-week-old plant grown in a greenhouse in Bleiswijk, the Netherlands, in February 2023. Colors in the photographs may differ from the color values cited in the detailed botanical description, which accurately describe the actual colors of the new variety.

DESCRIPTION OF THE NEW VARIETY

Figure 1:
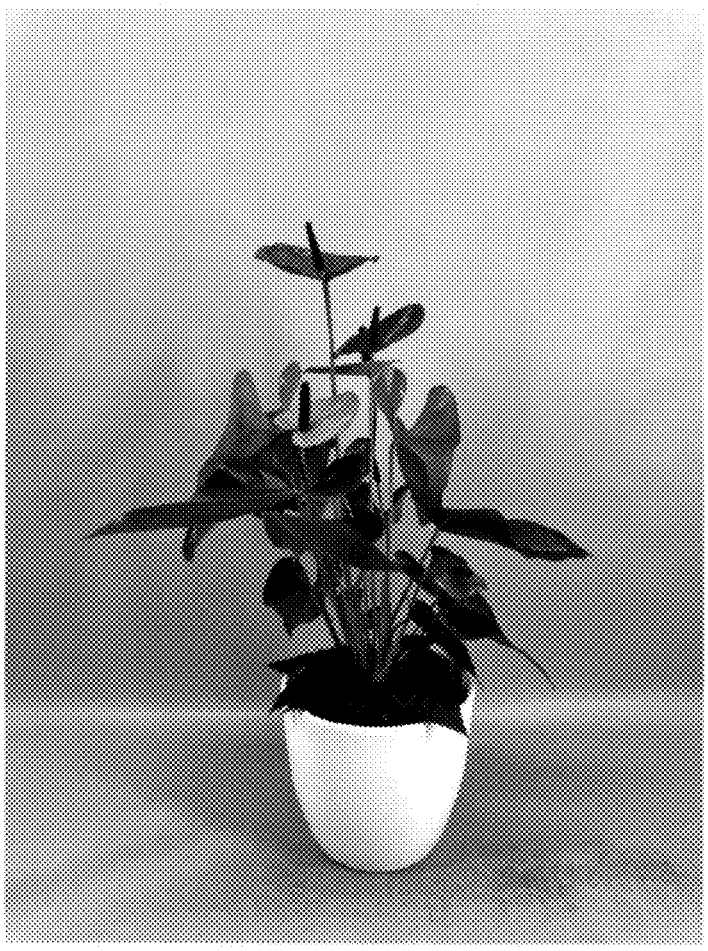
FIG. 1 shows the overall plant habit, including blooms, buds, and foliage.
Figure 2:
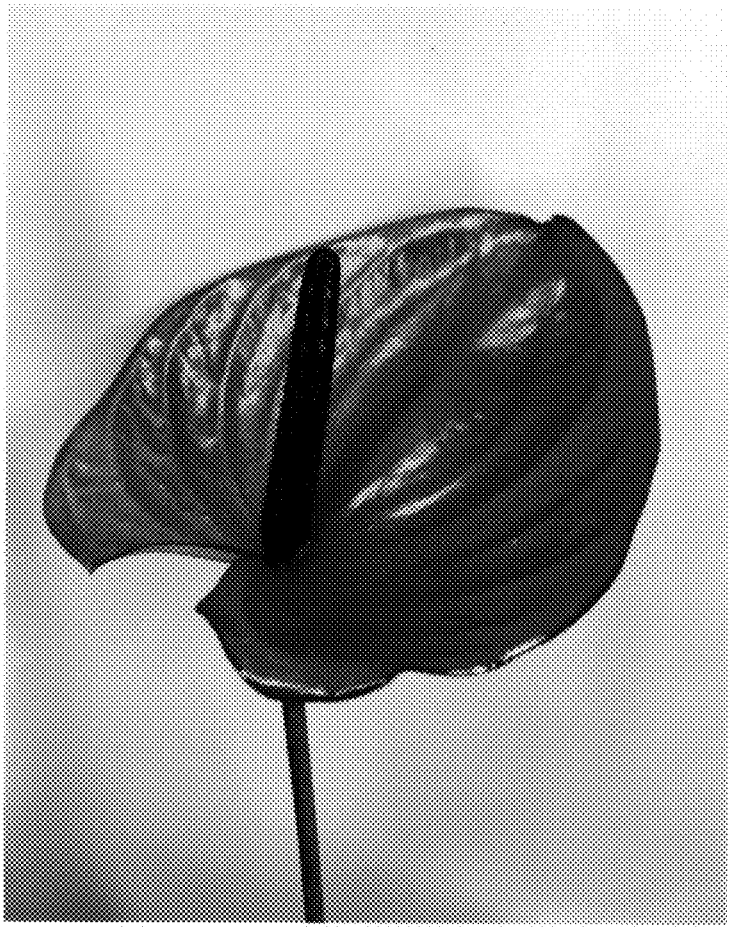
FIG. 2 shows a close-up of the mature spathe.
Figure 3:
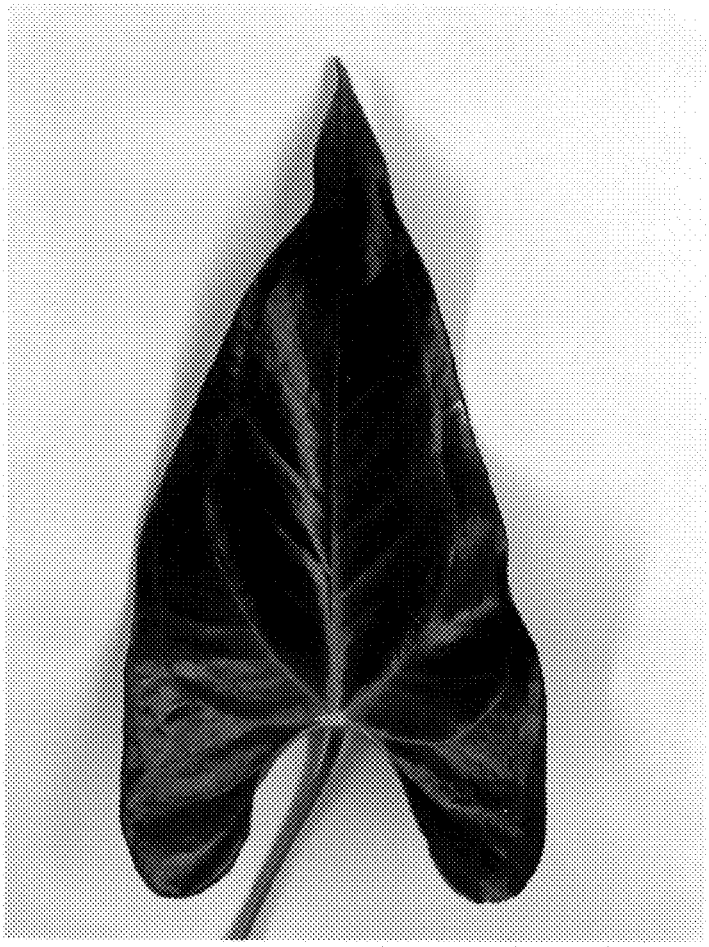
FIG. 3 shows a close-up of the upper leaf blade surface.

The following detailed description sets forth the distinctive characteristics of 'AN2891370'. The data which define these characteristics were collected from asexual reproductions carried out in Bleiswijk, the Netherlands. The plant history was taken on 52-week-old plants which were planted from tissue culture in 17-centimeter (diameter) pots and grown in a glass greenhouse between 19° C. and 24° C. Observations were made in February 2023. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'AN2891370'.

Parentage:

*Female parent*.—*Anthurium* plant '25528-07' (unpatented).

*Male parent*.—*Anthurium* plant '25414-03' (unpatented).

Plant:

*Propagation*.—Tissue culture.

*Root description*.—Fleshy-creamy (RHS 158D) colored roots with a pink shade (RHS 37C) and small hairy lateral roots having greenish-yellow (RHS 6A) colored root tips.

*Time to produce a finished flowering plant*.—50 to 54 weeks after planting in a 17-cm (diameter) pot.

*Growth habit*.—Upright.

*Height* (*measured from soil, including inflorescence*).—38.0 cm to 43.0 cm.

*Width* (*measured from leaf tips*).—34.0 cm to 37.0 cm.

Leaves:

*Immature leaves*.—Length: 20.0 cm to 23.0 cm. Width: 10.0 cm to 12.0 cm. Color: Upper surface: RHS 146A. Lower surface: RHS 146B. Texture (both upper and lower surfaces): Glossy, leathery, and thin.

*Mature leaves*.—Length (fully expanded): 23.0 cm to 26.0 cm. Width: 12.0 cm to 14.0 cm. Shape: Narrowly long cordate. Apex: Abruptly acuminate. Base: Cordate. Leaf blade angle with the petiole: Between 70 degrees and 90 degrees. Leaf margin: Entire. Color: Upper surface: RHS 147A. Lower surface: RHS 146A. Texture: Upper surface: Strongly glossy, leathery, and thick. Lower surface: Glossy, leathery, and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Present. Arrangement: Leaf blade has two lobes extending past the petiole. The lobes are non-touching. Length of lobes of mature leaf blades: 3.0 cm to 3.5 cm. Width of lobes of mature leaf blades: 4.0 cm to 5.0 cm. Distance from petiole/leaf junction to highest point on lobes of mature leaf blades: 6.0 cm to 7.0 cm.

*Petiole*.—Cross-section: Round. Diameter: 0.4 cm to 0.5 cm. Length: 23.0 cm to 26.0 cm for a mature leaf size. Color: Mature leaf: RHS 144A. Immature leaf: RHS 144B. Cataphyll color surrounding the petiole: Outside: RHS 145B with purplish-red tip (RHS 70A). Inside: RHS 145D.

*Geniculum*.—Length: 2.5 cm to 3.0 cm. Width: 0.5 cm to 0.6 cm. Color: RHS 146B.

Inflorescence:

*Arrangement*.—Single.

*Flowering habit* (*length of flowering season*).—Continuous.

*Number of inflorescences per plant*.—6 to 7 flowers in a period of one year.

*Fragrance*.—Absent.

*Longevity of inflorescence on plant*.—About half year.

Spathe:

*Buds*.—The spathe is tightly rolled around the spadix and extrudes from the peduncle sheath. After the spathe is fully opened, the peduncle elongates some extra centimeters.

*Arrangement*.—Spathe angle with the peduncle is between 110 degrees and 130 degrees; the spathe stands on a wiry peduncle about 4.0 cm to 7.0 cm above the foliage.

*Shape*.—Oblong cordate.

*Apex*.—Mucronate.

*Base*.—Cordate.

*Texture*.—Medium blistered and medium glossy.

*Margin*.—Weakly undulated.

*Size*.—Length: 11.5 cm to 12.5 cm. Width: 11.0 cm to 12.0 cm.

*Lobes*.—Present. Arrangement: The spathe has two lobes extending past the peduncle. The lobes non-touching. Length: 2.0 cm to 3.0 cm. Width: 4.5 cm to 5.5 cm.

*Color*.—Just fully open: Upper surface: RHS N79C. Lower surface: RHS N77B. This dark purplish-red color remains for about 8 weeks. After that, spathe turns pink (RHS 185D).

Peduncle:

*Shape*.—Erect.

*Cross-section*.—Round.

*Length*.—36.0 cm to 39.0 cm.

*Diameter*.—0.4 cm to 0.5 cm.

*Color*.—RHS 144B with a touch of dark red (RHS 187C) toward the spathe.

Flowering time:

*General*.—One small, rooted, untreated tissue culture plant of 8.0 cm tall will flower for the first time, depending on the season, after 50 to 52 weeks and 5 to 6 blossoms appear. More blossoms appear after some additional weeks so that a full-flowering and commercial plant will have 6 to 7 dark purplish-red spathes. Smaller blossoms may occur on immature plants.

Spadix:

*Size*.—Length: 5.0 cm to 6.0 cm (depending on flower size). Width (at apex): 0.6 cm to 0.7 cm. Width (at base): 0.7 cm to 0.8 cm.

*Shape*.—Columnar.

*Angle of spadix tip with peduncle*.—160 degrees to 170 degrees.

*Texture*.—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color*.—Immature: (RHS N186B). Mature: RHS N186B. Ages to: RHS N77A.

Flowers:

*Quantity per spadix*.—180 to 210.

*Spadix flower arrangement*.—Bisexual, rounded in cross-section.

*Shape*.—Rounded.

*Size*.—Length: 0.05 cm to 0.1 cm. Diameter (maximum): 0.10 cm.

*Color*.—RHS N79C.

Reproductive organs:

*Stamens*.—Not visible.

*Pollen amount*.—Absent.

*Pistil*.—Quantity: 180 to 210. Length: Less than 0.01 cm. Color: RHS N79C.

*Style*.—Not observed to date.

*Stigma*.—Shape: Ovoid. Diameter: Less than 0.01 cm. Color: RHS N79C.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2891370' differs from the female parent plant '25528-07' (unpatented) in that 'AN2891370' has a dark purple spadix, basal and distal part, and dark purplish-red spathes, whereas '25528-07' has a white spadix on the basal part and greenish-yellow spadix on the distal part, and light purple spathes.

'AN2891370' differs from the male parent plant '25414-03' (unpatented) in that 'AN2891370' has medium spadices that are weakly incurved and narrowly-long, cordate leaves, whereas '25414-03' has long spadices that are straight and elliptical-cordate leaves.

'AN2891370' differs from similar commercial variety 'ANTHDUBAQ' (U.S. Plant Pat. No. 27,889) in that 'AN2891370' has large, oblong-cordate spathes with medium blistering, and medium spadices, whereas 'ANTHDUBAQ' has small, ovate spathes with very weak to weak blistering, and very short to short spadices.

'AN2891370' differs from similar variety 'ANTHCOMEOR' (unpatented) in that 'AN2891370' has large, oblong-cordate spathes that have an obtuse angle of the distal part of the peduncle, whereas 'ANTHCOMEOR' has medium, orbicular-cordate spathes that have an approximate right angle of the distal part of the peduncle.

I claim:

1. A new and distinct variety of *Anthurium* plant named 'AN2891370', substantially as illustrated and described herein.

* * * * *